United States Patent [19]

Hatch

[11] 4,051,373
[45] Sept. 27, 1977

[54] DELAY LINE CLIPPING IN A SCINTILLATION CAMERA SYSTEM

[75] Inventor: Kenneth F. Hatch, Prospect, Conn.
[73] Assignee: Picker Corporation, Cleveland, Ohio
[21] Appl. No.: 599,657
[22] Filed: July 28, 1975

Related U.S. Application Data

[63] Continuation of Ser. No. 478,200, June 11, 1974, abandoned.

[51] Int. Cl.² ........................ G01T 1/164; G01T 1/20
[52] U.S. Cl. ................................ 250/363 S; 250/369
[58] Field of Search .......................... 250/363 S, 369

[56] References Cited

U.S. PATENT DOCUMENTS

| 2,778,949 | 1/1957 | Borkowski et al. | 250/369 |
| 3,573,458 | 4/1971 | Anger | 250/369 X |
| 3,582,651 | 6/1971 | Siedband | 250/363 |
| 3,860,821 | 1/1975 | Barrett | 250/363 S |
| 3,916,198 | 10/1975 | Coltman et al. | 250/363 S |

*Primary Examiner*—Archie R. Borchelt
*Attorney, Agent, or Firm*—Watts, Hoffmann, Fisher & Heinke Co.

[57] ABSTRACT

A scintillation camera system including compensated delay line clipping circuitry for narrowing data representing pulses in the system without introducing base line undershoot and a restoring circuit for minimizing base line fluctuation of a data signal. The compensated circuitry includes a single delay line circuit for clipping an incoming data pulse having a relatively long trailing edge. A variable resistor is coupled with the circuit for controlling amplitude and polarity of the unclipped, incoming data pulse. A value of this unclipped pulse is controllably summed with the clipped pulse for correcting delay line attenuation and base line undershoot. The restoring circuit is combined with the single delay line clipping circuit for restoring the base line of the single delay line clipped pulses. The restoring circuit produces double delay line clipped timing pulses from the single delay line clipped waveform pulses. The circuit includes a restoring gate connecting a data line coupling capacitor to circuit ground. The gate is responsive to the double delay line clipped timing pulses for allowing selective discharging of the coupling capacitor in anticipation of a data pulse for maintaining the base line of the data pulse.

17 Claims, 10 Drawing Figures

DELAY LINE CLIPPING IN A SCINTILLATION CAMERA SYSTEM

CROSS REFERENCED APPLICATION

This is a continuation of U.S. application Ser. No. 478,200 filed June 11, 1974 entitled DELAY LINE CLIPPING IN A SCINTILLATION CAMERA SYSTEM, now abandoned.

BACKGROUND OF THE INVENTION

This invention relates to scintillation camera systems and more specifically to scintillation camera systems having high speed pulse shaping circuitry for minimizing base line fluctuation and voltage undershooting.

In the diagnosis of certain illnesses, radioactive isotopes are administered to the patients. These isotopes have the characteristic of concentrating in certain types of tissue. The degree of concentration in the tissue is dependent upon tissue type. For example, iodine 131 generally collects or concentrates in the tissue of the thyroid gland. Upon detection of the level or radioactive isotope concentration and presentation of this detected information on a suitable readout device, such as an oscilloscope, it is frequently possible to diagnose the condition of the tissue under examination.

One well known type of device for detecting levels of radioisotope concentration is the scintillation camera system. Scintillation cameras generally incorporate a relatively large disc-shaped scintillation crystal which is positioned so that the crystal intercepts gamma radiation emitted by a patient under study. The crystal scintillates in response to impinging gamma ray energy to provide pulses of light energy. A thallium activated sodium iodide crystal is typically employed as the scintillation crystal.

A plurality of phototubes are positioned adjacent the crystal so that a scintillation occurring in the crystal is normally detected by several of the phototubes. Each of the detecting phototubes develops in response to the scintillation an electrical signal having an amplitude proportional to the intensity of the light energy received by it. The signals developed by the phototubes are then amplified and applied to appropriate electronic computing circuitry for developing electrical signals representative of the position of the light pulse or scintillation. The intensity of the signal is threshold detected by a process commonly referred to as pulse height analysis to determine whether the signals represent photopeak scintillations resulting from a gamma ray originatng from the isotope which has been administered to the patient. The signals developed by the phototubes are typically preamplified to provide signals having relatively narrow pulse widths to enable as high a processing rate as possible. One such gamma ray imaging camera system is disclosed in U.S. Pat. No. 3,683,180 issued Aug. 8, 1972.

At high counting rates this type of camera system has several difficulties which have hindered high speed operation. Coupling capacitors used for transmission of the data pulses are intermittently charged and discharged by the pulse bursts passing through the capacitors. This results in considerable base line bounding and lessens the fidelity of data detection. Because these pulses are pulse height analyzed by threshold detectors, base line bouncing tends to introduce pulse height detection errors.

Scintillation camera systems now commonly utilize delay line clipping techniques for narrowing the pulse width of the data pulses for obtaining higher counting rates with minimum distortion of the pulse amplitudes.

Known delay line clipping circuits utilize a delay line to couple the pulse transmission line to circuit ground. One input of a differential amplifier is coupled to the pulse transmission line and to the delay line while the other input of the differential amplifier is coupled to circuit ground. When using an ideal delay line, ideal resistors, and ideal amplifiers, a step input pulse is shortened to a square pulse of width twice the delay time of the delay line. Since delay lines have unavoidable attentuation and are not ideal, the base lines of the clipped pulses do not return to the original value. After the clipping they exhibit an offset proportional to the original step input voltage and to the delay line attenuation. Furthermore, since the input pulse is finite with a decaying trailing edge rather than a step, the resultant clipped pulse frequently undershoots the base line voltage.

Attempts have been made in systems other than scintillation camera systems to remove the base line fluctuations of single delay line clipped pulses. One such base line restoring circuit is that often referred to as an amplified diode restorer. Due to the finite forward breakover voltage of a diode restorer, even upon amplification, the restorer is unable to work properly below a threshold voltage of approximately 30 millivolts. This level of threshold voltage is unacceptable in radiation imaging systems as accurate pulse intensity data is required down to substantially zero volts. The accurate detection of such small voltages is required if the situs of respective scintillations is to be accurately reconstructed.

Double delay line clipping networks have been utilized to narrow pulses which have relatively long exponential fall times in nuclear spectroscopy systems. It is known that such double delay line clipped pulses are advantageous in certain respects over comparable single delay line clipped pulses. That is, the total charge deposited on any coupling capacitor in the date transmission line due to passage of each pulse is zero because the double delay line pulse exhibits equal energies above and below the base line. Accordingly, the average base line value is relatively constant; whereas, the single delay line clipped pulse exhibits a base line which is astable at high rates due to random time variations in the average charge passing through coupling capacitors.

Double delay line clipped pulses have their disadvantages when used as data pulses in a scintillation camera system. For example, for a given pulse duration the effective integration time of the photomultiplier tube generating the pulse is reduced. Conversely, if the integration time is kept equal to that of a single delay line clipped pulse, the total pulse duration is lengthened, resulting in a slower operating system.

On the other hand, double delay line data pulses are ideal timing pulses. The pulse widths may be sufficiently narrow to accommodate high frequency data pulses separated by as little as 1.5 microseconds. Because the base line of a double delay line pulse is stable, restoring circuitry is unneeded.

The present invention overcomes the above noted and other disadvatages by providing a novel base line restoring circuit and a novel delay line clipping circuit in a scintillation camera system. Single and double delay line clipped signal waveforms are generated for increasing the operational frequency and fidelity of data detection of the camera system which is otherwise degraded by base line distortion such as undershooting, overshooting, and capacitive build-up.

The camera system includes a set of photomultiplier tubes and associate amplifiers which generate sequences of pulses. These pulses are pulse-height analyzed for detecting a scintillation having an energy level which falls within a predetermined energy range. Data pulses which have the predetermined energy are said to represent photopeak events of the isotope which has been administered to the patient. These data pulses are combined to provide $x+$, $x-$, $y+$, $y-$ coordinate data representative of the situs of a photopeak event and to provide Z energy data representative of the energy of the photopeak event. The pulses are characteristically produced having a relatively long decaying trailing edge by dynamic biasing of the preamplifier. The preamplifiers are biased out of saturation over all ranges of pulse energy levels and count rates.

Single delay line clipping circuitry is provided for narrowing the pulse width of the decaying electrical data pulses which increase operating speed the occurrence of data loss. According to one aspect of the invention, the clipping circuitry is compensated and includes a variable resistance element which controls magnitude and polarity of portions of an unclipped data pulse and adds these portions to a delay line clipped data pulse for substantially eliminating undershooting base line voltage.

In another embodiment, a novel base line restorer circuit is provided which is advantageously used prior to any thresholding to the data pulses to allow precise amplitude analysis. The restorer circuit requires timing pulses which are derived from double delay line type pulses, because of their inherently stable base line. The single delay line clipping circuitry is combined in a novel circuit for providing double delay line type pulses without the requirement of a second delay line. The delay line of the single delay line clipping circuitry for the energy channel is simultaneously used for generating the double delay line pulses. The double delay line pulses are substantially synchronized in time with the single delay line clipped data pulses and are used as timing pulses.

The base line restorer circuit includes a gating element and a coupling capacitor connected in series with a data line over which the data pulses are transmitted. The gating element is responsive to the double line clipped timing pulse for selectively coupling the data line to a reference potential such as circuit ground. This discharges the coupling capacitor in anticipation of a data pulse and thereby provides the single delay line shaped pulses with improved base line voltage characteristics.

It accordingly is a general object of this invention to provide a scintillation camera having novel and improved pulse-shaping clipping circuitry for maximizing system speed without incurring data loss.

Other objects and advantages and a fuller understanding of the invention may be obtained by referring to the following detailed description when read in conjunction with the accompanying drawings.

DESCRIPTION OF THE PREFERRED EMBODIMENTS

Figure 1:
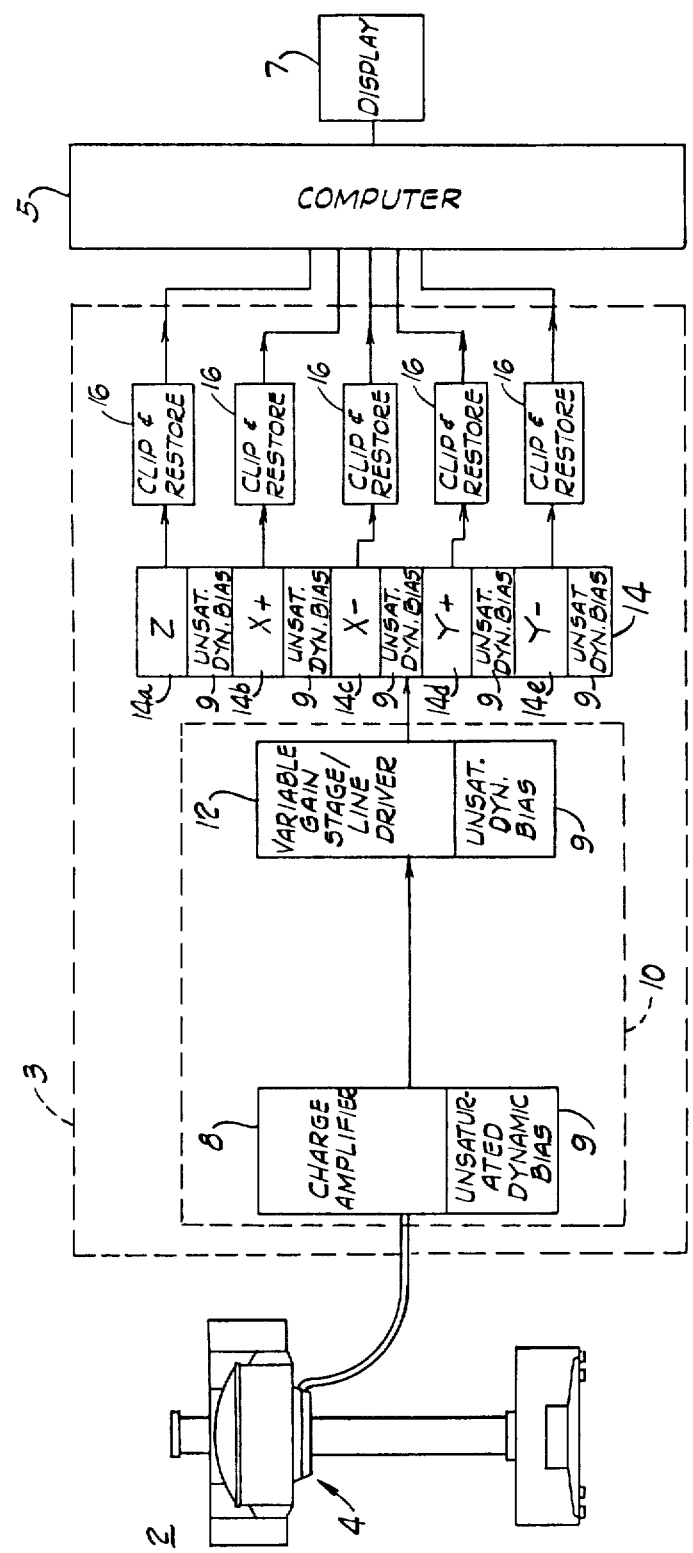
FIG. 1 is a part pictorial, partially functional representation of a scintillation camera system which embodies the invention.

Referring now to FIG. 1, a radiation imaging detection system is depicted which embodies the present invention. The radiation system generally includes a radiation detector unit 2 coupled to data processing circuitry 3. Radiation impinging upon the detector head 2 causes the generation of signals which are converted by the data processing circuitry 3 into meaningful pulse data relating to the study. A computer 5 and a display mechanism 7 are also provided. The computer 5 converts the pulse data into a form required by the display mechanism 7. The display mechanism 7 produces an image representative of the radiation striking the detector head 2. The computer 5 and the display mechanism 7 are conventional and are described in U.S. Pat. No. 3,697,753, Scintillation Camera Having a Variable Gain Plural Amplifier System, issued Oct. 10, 1972.

The detector head 2 includes a large scintillation crystal of thallium sodium iodide and a collimator 4 which is positioned between a subject under study (not shown) and the crystal. The detector head 2 further includes a plurality of photomultiplier tubes positioned adjacent the crystal. Conventionally there are nineteen tubes, and they generate electrical pulses in response to crystal scintillations that are generated by radiation impinging upon the crystal. The detector head 2 is explained in detail in U.S. Pat. No. 3,784,819, issued Jan. 8, 1974.

The signals from the phototubes in the detector head 2 are coupled to the data processing circuitry 3. The data processing circuitry 3 includes an amplifier section 10, a decoder matrix 14, and clip and restore circuitry 16. The amplifier section 10 includes a charge preamplifier section 8 and a variable gain stage, line driver section 12, both of which are conventional. The sections 8, 12 are of the charge amplifier/ RC differentiation type. They generate pulses having typically a 220 nanosecond rise time constant and a 10 microsecond fall time constant. Dynamic biasing circuitry 9 is provided for biasing the amplifier for unsaturated operation over all ranges of energy levels and pulse rates.

It has been found advantageous to increase the fall time constant of the pulses to approximately 10 microseconds from the conventional 1 microsecond fall time.

These pulses having a relatively long trailing edge are subsequently clipped to provide pulses having width of approximately 2 microseconds. The described pulse-shaping arrangement allows approximately 99% of the scintillation energy to be captured by the photomultiplier tubes and transmitted.

The 10 microsecond data pulses from the amplifier section 10 are input into the decoder matrix 14 whereby a plurality of coordinate channel signals $x+$, $x-$, $y+$, $y-$ and an energy channel Z are generated in decoders 14a-14e respectively. More specifically, the nineteen photomultiplier tubes in the detector head 2 actuates section 10, whose outputs are coupled to the decoder matrix 14. The decoder matrix 14 appropriately combines the data pulses according to location of the phototubes to provide the coordinate and energy information. This information characterizes the situs and strength of the photopeak event. The decoder matrix 14 is now well known in the art, and its operation is readily understood.

The data representing coordinate and energy channel information from the decoder matrix 14 is input into the clip and restore circuitry 16 for wave-shaping and base line restoring, according to an important embodiment of the invention. The data pulses having a 10 microsecond fall time are clipped to provide pulses having an approximate 2 microsecond width. This has advantageously proven to minimize pulse pile-up, but has also proven to maintain data fidelity. The clip and restore circuitry 16 is shown and explained in detail in FIG. 2.

The data pulses output from the clip and restore circuitry 16 are input into the computer circuitry 5 where various stages of threshold analysis of the data pulses is performed. The circuitry 5 includes delay circuitry, pulse-stretching circuitry, and pea detectors, and ratio circuits (all of which are not shown). This circuitry is conventional and conforms the data for eventually reconstructing an image of the object under study on the display mechanism 7, which is an oscilloscope or recorder.

Figure 2:
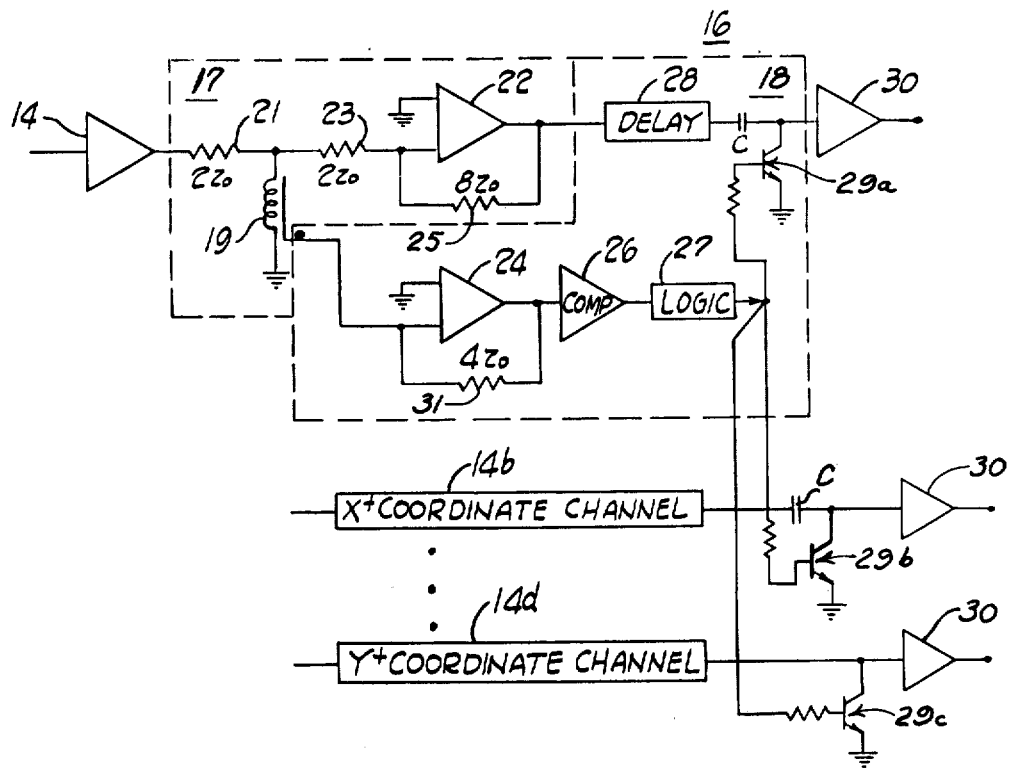
FIG. 2 is a schematic of single and double delay line pulse-shaping clipping circuitry in accordance with an aspect of the invention for restoring the base line voltage of single delay line clipped data pulses.

Referring now to FIG. 2, a preferred embodiment of the clip and restore circuitry 16 is shown. The circuit 16 includes a single delay line clipping circuit 17 and a restoring circuit 18. The clipping circuit 17 is of a generally conventional design for a single delay line clipping circuit, and comprises a delay line 19 coupled to a data input line of a differential amplifier 22. A pair of resistors 21, 23 of value twice the magnitude of the characteristic impedance, Zo, of the delay line 19 are serially connected in the data input line of the amplifier. The delay line 19 is coupled between circuit ground and the common connection of the resistors 21, 23. A feedback resistor 25 of value 8 Zo is connected between the output of the amplifier 22 and the data input line.

Figure 4A:
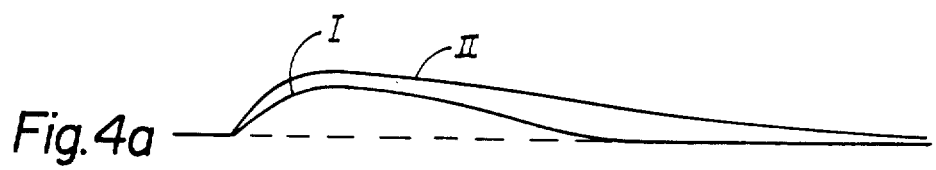
FIG. 4a is a graphical representation of a prior art waveform.

The wave-shaping effect of the clipping circuit 17 is seen when viewing FIG. 4. Waveform I in FIG. 4a depicts a conventional prior art data pulse having a 220 nanosecond rise time constant and one microsecond fall time constant. The disadvantage of a pulse having this waveform is that such a pulse requires a relatively long time to decay fully to the base line. Not only does such a pulse having a large width reduce system speed, but it induces base line instability.

Figure 4B:
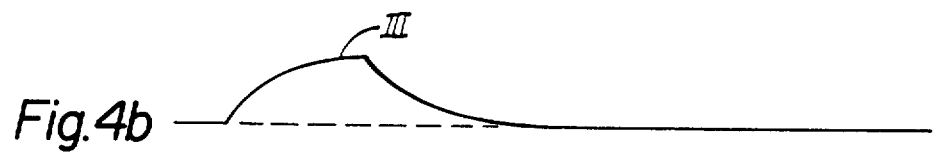
FIG. 4b is a graphical representation of a simple delay line clipped waveform.
Figure 4C:
FIG. 4c is a graphical representation of a double clipped pulse waveform.

Waveform II in FIG. 4a has a ten microsecond fall time constant, as produced by the amplifier section 10 in FIG. 1. Data pulses having this waveform are input into the clipping circuit 17 which generates a single delay line clipped pulse, waveform III. As seen in FIG. 4b, waveform III exhibits a sufficiently wide pulse width to characterize the data from the photomuliplier tubes, yet it exhibits a sufficiently narrow pulse width to enable high speed system operation.

Because a single delay line clipped pulse, such as waveform III, causes base line fluctuation and instability, the restoring circuit 18 is utilized. The restoring circuit 18 assures maintenance of a steady base line for allowing precise amplitude determination by the thresholding circuitry in the computer circuitry 5.

Referring again to FIG. 2, the restoring circuit 18 includes a feedback amplifier 24, a comparator 26 and a logic gate 27 which is serially connected to an output terminal of the comparator 26. A set of base line restoring elements in the form of restoring transistors 29a-29e is also provided. The amplifier 24 has a feedback resistor 31 connecting the output terminal to a data input terminal. The data input terminal is directly connected to the shield of the delay line 19. This causes a double delay line clipped waveform to be generated by the amplifier 24. Since amplifier 24 presents a virtual ground to the delay line shield, it does not affect the operation of the single delay line stage 17.

A delay mechanism 28, a coupling capacitor C, and an output buffer amplifier 30 are serially connected to the output of the amplifier 22 for providing the single delay line clipped waveform. The delay mechanism 28 delays the arrival of the single delay line clipped data pulse at the coupling capacitor C. It is delayed until the logic signal generated by the double line clipped pulse arrives at the restoring transistors 29a-29e. The coupling capacitors C in conjunction with the gating transistors 29a-29j remove high speed, A.C. base line fluctuations from the data pulses.

The amplifier 24 functions as a current to voltage converter for generating the double clipped pulse. The input current to the amplifier 24 is the return current in the delay line shield. Shield current is "out" of the delay line shield for the first half of the delay line shield output pulse, and is "into" the delay line shield during the second half of the output pulse. This cause the amplifier 24 to generate double clipped pulse shown in FIG. 4C.

Because amplitude information is not important at the output of the amplifier 24, a double delay line clipped signal is ideal. The base line of a double clipped pulse is self-restoring and does not deviate with pulse occurrence. That is, as seen from FIG. 4C, the voltage waveform exists an equal amount of time above the base line as it does below the base line, so that the net charge on the line is substantially zero.

If the restoring transistors 29 are not employed, variations in the average charge passing through the coupling capacitor C, or any other signal coupling capacitor, generate base line variance due to the randomness of pulses. This base line variation introduces detection errors in the processing circuitry and produces false output information describing the organ under study.

The restoring transistors 29a-29e are gated conductive by the double delay line timing pulses to overcome this problem. When the transistors 29 are selectively gated conductive, they clamp the output side of the series coupling capacitor C to ground. If there is any residual charge accumulated in the capacitor C from the passage of a previous pulse, accumulation is discharged by the connection to circuit ground. When a pulse arrives at the output of the delay mechanism 28, a corresponding double clipped pulse also arrives at the logic gate 27 which renders the restoring transistors inoperative removing the connection to circuit ground.

Nonconductance of any restoring transistor 29 momentarily leaves the output side of the capacitor discharge (or i.e. the output side is charged to the base line voltage immediately preceding the data pulse). The pulse arriving at the output of the delay means 28 is coupled through the capacitor C except that it is substantially unaffected (since the gate transistors 29 are now open), referenced to zero volts. Buffer amplifier 30 presents a very high load impedance to the capacitor for insuring that the pulses pass through capacitor C without substantially charging them. Since the output side of serially connected coupling capacitor C has been clamped at circuit ground, the buffer amplifier 30 faithfully reproduces the pulse starting from zero volts, regardless of the base line value of the signal at the output of the delay mechanism 28.

The logic signal generator for the restoring circuit, items 24, 26, 27 and 31, are employed only in the clip and restore circuitry 16 of the Z energy channel. The $x+$, $x-$, $y+$, $y-$ coordinate channels only have the restoring transistors 29b-29d and capacitors C connected to their respective delay elements 28. The Z energy channel is chosen to drive the restoring transistor 29 because photopeak events of interest generate pulses in the energy channel above a minimum, detectable level such as 100 millivots. This level is a threshold for triggering the logic circuit that drives the restoring transistors 29a-29e in the coordinate channels and Z channel. This signal will always have an amplitude greater than 100 millivolts when the impinging data is accepted as valid. Thus the resistorers all operate accurately even when respective coordinate signals have even a zero magnitude. As is understood in radiation impinging systems, such small level data pulses in the coordinate channels must be accurately detected if precise situs reconstruction of the scintillation event is to be realized. Therefore, the Z energy channel in a radiation detection system is particularly well suited for driving the base line restoring circuitry 18.

Figure 3:
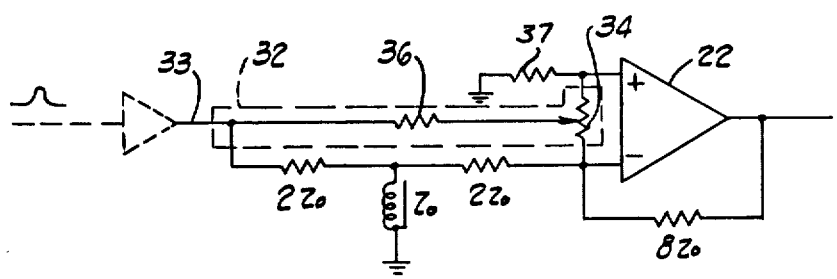
FIG. 3 is a schematic of pulse-shaping clipping circuitry for eliminating base line voltage undershoot and base line voltage offset in accordance with another aspect of the invention.

Referring now to FIG. 3, there is shown an improved single delay line clipping circuit which features compensation for voltage undershoot or positive tail. The improved single delay line clipping circuit is similar to that referenced at 17 in FIG. 2, but features a compensating circuit 32. Similar functional elements in the clipping circuits of FIG. 2 and FIG. 3 have like numbers and are not further described.

The compensating circuit 32 comprises resistive elements 36, 37 and a variable resistance element 34 coupling the unclipped data signal on an input line 33 to the input signals of amplifier 22 and ground. In the illustrated eembodiment the variable resistance element is a potentiometer 34 which is coupled to the input terminals of the amplifier 22, and is coupled to receive the unclipped signal on its wiper terminal, through resistor 36, coupled to the input line 33. It has a value determined by the desired range for compensating for the attenuation of the delay line and the delay line constants of the incoming signal. The potentiometer 34 provides a single control for uniformly correcting delay line attenuation and base line voltage undershoot of the clipped data pulse in one continuous adjustment.

Figure 5A:
FIG. 5a is a graphical representation of a stepped input voltage.
Figure 5B:
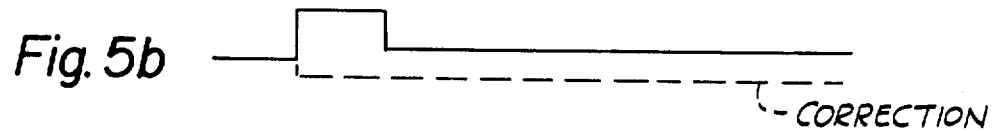
FIG. 5b is a graphical representation of a waveform exhibiting a positive offset.
Figure 5C:
FIG. 5c is a graphical representation of an input pulse exhibiting decay phenomena.
Figure 5D:
FIG. 5d is a graphical representation of a clipped pulse exhibiting undershoot

More specifically, because delay lines, resistors and differential amplifiers are nonideal, and because the input data pulses are not purely step function pulses, i.e., they do exhibit decaying tails, the clipped output data pulse waveform is less than ideal. Due to attenuation by the delay line, step input voltage (FIG. 5a), after clipping, fails to return to the base line and exhibits a positive offset (FIG. 5b). This offset is proportional to the original step input voltage and to the delay line attenuation. On the other hand, if the delay line attenuation is negligible because the input pulse is not a step but exhibits a decaying tail (FIG. 5c), the resultant clipped pulse exhibits undershoot (FIG. 5d). The compensating circuit 32 corrects for both conditions in one continuous adjustment.

Adjustment of the potentiometer 34 modifies the unclipped data pulse so that output base line undershooting and offset of the clipped data pulse is substantially eliminated. If the potentiometer 34 is set to one extreme position for the resistive element 37, a maximum portion of the unclipped signal input via the wiper terminal is sumed in amplifier 27 with the clipped signal passing through the resistor 23 to correct undershooting. By way of example, the unclipped pulse on the input line 33 has a relatively long fall time constant, such as 10 microseconds and exhibits a decaying pulse above the base reference potential of the line (FIG. 5c). Because the undershoot (FIG. 5d) is a similar but opposite magnitude, addition of the two signals results in an output signal having substantially zero voltage offset. By setting the potentiometer 34 to the other extreme position, a maximum portion of the input signal, determined by the resistance element 36, is summed in the opposite polarity with the clipped pulse to correct for delay line attenuation.

Although the invention has been described in its preferred form with a certain degree of particularity, it is understood that such particularity has been for example only. Numerous changes in the details of construction and changes in the combinations and arrangements of the parts will be hereafter obvious without departing from the spirit and scope of the invention.

What is claimed is:

1. In a scintillation camera system having scintillator means for producing scintillations in response to impinging radiation, light responsive means responsive to the scintillations for generating sequences of data signals representative of radiation impinging on a respective portion of said scintillator means, signal processing circuitry including pulse shaping circuitry responsive to the data signals for generating a plurality of data pulses defining the situs of respective scintillations and a display mechanism for producing images representing the radiation impinging on the scintillator means, the improvement wherein the pulse-shaping circuitry comprises a compensating circuit means including circuitry coupled to produce and combine first signals representing data signals and second signals representing data pulses for decreasing base line fluctuation of the data pulses and thereby improving pulse detection.

2. The scintillation camera system according to claim 1 wherein the pulse-shaping circuitry includes a clipping circuit having an input coupled to a data line and an output for clipping the data pulses.

3. The scintillation camera system according to claim 2 wherein said compensating circuit means further includes:

a. differential amplifier means having first and second input terminals, said first input terminal coupled to a first reference potential; and, b. resistor means coupling said second input terminal to the output of said clipping circuit and to said data line.

4. The scintillation camera system according to claim 3 wherein said clipping circuit includes a delay line resistively coupling said data line and said second input terminal to a second reference potential.

5. The scintillation camera system according to claim 3 wherein said resistor means further includes a potentiometer having its fixed resistance terminals coupling said first and second input terminals, and having it wiper terminal coupled to said data line.

6. The scintillation camera system according to claim 5 and further including resistor coupling said wiper terminal to said data line.

7. The scintillation camera system according to claim 1 wherein said compensating circuit means includes a capacitive element serially connected to a data line and a gating element selectively coupling said capacitive element to a reference potential.

8. The scintillator camera system according to claim 3 wherein said compensating circuit means includes:
  a. means coupled to said clipping circuit for providing a double delay line clipped timing signal;
  b. a capacitive element serially coupled to said data line; and,
  c. a gating element responsive to said timing signal for selectively coupling said capacitive element to a reference potential.

9. In a scintillation camera system having scintillator means for producing scintillations in response to impinging radiation, a plurality of amplifier drivers responsive to the scintillations for generating electrical pulses having amplitudes representative of radiation impinging on a respective portion of said scintillator means, and signal processing circuitry responsive to the electrical pulses for generating a plurality of data signals, said signal processing circuitry containing a plurality of coordinate signal amplifier driven lines for indicating coordinate information of the scintillation, and an energy signal amplifier driven line for indicating the energy magnitude of the scintillation, the combination including base line amplitude restorer means coupled to the energy signal and coordinate signal amplifier drivers, said base line amplitude restorer means comprising:
  a. a timing signal generator responsive to at least one of the energy and coordinate signal amplifier driven lines to produce a timing signal in response to the occurrence of a radiation scintillation; and
  b. gating means coupling at least one of said coordinate signal lines to a reference potential in response to said timing signal for conditioning the signal processing circuitry for operation in anticipation of receipt of data representing a scintillation.

10. The scintillation camera system according to claim 9 wherein gating means includes transistor switching means selectively coupling said energy channel line to said reference potential in response to said timing signal.

11. The scintillation camera system according to claim 10 wherein said transistor switching means includes a plurality of transistors selectively coupling said coordinate channel lines to said reference potential, in response to said timing signal.

12. A radiation camera system comprising a radiation detector, a plurality of amplifier driven coordinate channel lines coupled to the detector for indicating the locus of a radiation event, an amplifier driven energy channel line for indicating the energy magnitude of the radiation event, delay line clipping means having a delay line coupling the output of the amplifier of said energy channel line to a reference potential, first differential amplifier means coupled to said delay line for providing a single delay line clipped voltage indicative of the magnitude of the respective radiation event; and a current sensing converter means coupled to a common of said delay line for sensing the current therein and cooperating with the delay line for generating double delay line clipped output pulses time synchronized with the single delay line clipped pulses and being indicative of the occurrence of a radiation event.

13. The scintillation camera system according to claim 12 wherein said gating means includes a plurality of transistor switching means coupling respective coordinate channel lines to said reference potential in response to said double delay line clipped output voltage.

14. The scintillation camera system according to claim 12 wherein said first differential amplifiers means includes a compensating circuit for summing a selected value of the unclipped data pulse with the clipped data pulse for minimizing voltage undershoot.

15. A method of operating a radiation camera system having a detector for producing radiation signals in response to impinging radiation, a plurality of amplifier drivers responsive to the radiation signals for generating electrical pulses having amplitudes representative of radiation impinging on a restrictive portion of said detector, and signal processing circuitry responsive to the electrical pulses for generating a plurality of data signals, said processing circuitry including a plurality of coordinate signal amplifier driven lines for indicating coordinate information of the radiation and an energy signal amplifier driven line for indicating the energy magnitude of the radiation, and a base line amplitude restorer coupled to the energy signal and coordinate signal amplifier drivers, said method comprising the steps of:
  a. producing a timing signal in response to the occurrence of a radiation event as sensed by signals transmitted by at least one of the energy and coordinate signal amplifier driven lines, and
  b. gating at least one of the coordinate signal lines to couple said coordiate signal line to a reference potential in response to said timing signal for conditioning the signal processing circuitry for operation in anticipation of receipt of data representing a radiation event.

16. In a radiation camera system having radiation sensitive structure for producing radiation indicating signals in response to radiation impinging on the radiation sensitive structure, and circuitry responsive to the radiation indicating signals for generating sequences of data signals representative of radiation impinging on the radiation sensitive structure, signal processing circuitry including pulse shaping circuitry responsive to the data signals for generating a plurality of data pulses defining the situs of respective radiations and a display apparatus for producing images representing the radiation impinging on the radiation sensitive structure, the improvement wherein the pulse-shaping circuitry comprises a compensating circuit including circuitry coupled to produce and combine first signals representing data signals and second signals representing data for decreasing base line fluctuations of the data pulses and thereby improving pulse detection.

17. In a radiation camera system having radiation sensitive structure for producing radiation indicating signals in response to radiation impinging on the radiation sensitive structure, a plurality of amplifier drivers responsive to the radiation indicating signals for generating electrical pulses having amplitudes representative of radiation impinging on said radiation sensitive structure, and signal processing circuitry responsive to the electrical pulses for generating a plurality of data signals, said signal processing circuitry containing a plurality of coordinate signal amplifier driven lines for indicating coordinate information of the impinging radiation, and an energy signal amplifier driven line for indicating the energy magnitude of the radiation event, a combination including base line amplitude restorer means coupled to the energy signal and coordinate signal amplifier drivers, said base line amplitude restorer means comprising:

a. a timing signal generator responsive to at least one of energy and coordinate signal amplifier driven lines to produce a timing signal in response to the occurrence of radiation impinging on the radiation sensitive structure; and b. gating means coupling at least one of said coordinate signal lines to a reference potential in response to said timing signal for conditioning the signal processing circuitry for operation in anticipation of receipt of data representing a radiation indicating signal.

* * * * *